(12) United States Patent  
Ross

(10) Patent No.: US 8,034,398 B2  
(45) Date of Patent: *Oct. 11, 2011

(54) SECURE TAG CODING

(75) Inventor: Gary A. Ross, Edinburgh (GB)

(73) Assignee: NCR Corporation, Duluth, GA (US)

( * ) Notice: Subject to any disclaimer, the term of this patent is extended or adjusted under 35 U.S.C. 154(b) by 1126 days.

This patent is subject to a terminal disclaimer.

(21) Appl. No.: 11/355,573

(22) Filed: Feb. 16, 2006

(65) Prior Publication Data

US 2007/0187630 A1    Aug. 16, 2007

(51) Int. Cl.  
B41M 3/14 (2006.01)  
B44F 1/12 (2006.01)

(52) U.S. Cl. .......................................................... 427/7
(58) Field of Classification Search ...................... 427/7  
See application file for complete search history.

(56) References Cited

U.S. PATENT DOCUMENTS

| 6,380,547 | B1 | 4/2002 | Gonzalez et al. | |
| 7,129,506 | B2 * | 10/2006 | Ross et al. | 250/556 |
| 7,378,675 | B2 * | 5/2008 | Ross et al. | 250/559.39 |
| 2002/0066543 | A1 | 6/2002 | Lilly | |
| 2007/0023521 | A1 * | 2/2007 | Wildey et al. | 235/454 |
| 2007/0095891 | A1 * | 5/2007 | Giering et al. | 235/379 |

FOREIGN PATENT DOCUMENTS

| EP | 0 922 498 A | 6/1999 |
| EP | 1491350 A2 * | 12/2004 |
| FR | 2 864 666 | 7/2001 |
| WO | WO 01/24107 A2 | 4/2001 |
| WO | WO 2004/038645 A1 | 5/2004 |
| WO | WO 2005/036480 A1 | 4/2005 |

* cited by examiner

*Primary Examiner* — Kelly M Gambetta  
(74) *Attorney, Agent, or Firm* — Paul W. Martin

(57) ABSTRACT

A secure tag coding method and device. The method comprises: providing a first type of secure tag having a first luminescence profile to indicate a first level code; providing a second type of secure tag having a second luminescence profile different from the first luminescence profile to indicate a second level code; mixing secure tags of the first type with secure tags of the second type in a predetermined ratio so that excitation of the mixed secure tags produces a composite of the first luminescence profile and the second luminescence profile, from which composite a multi-level code can be ascertained; and applying the mixture of first and second types of secure tags to a substrate. The substrate carrying this secure tag coding arrangement provides multi-level codes. The device for selecting and applying the secure tag coding arrangement to the substrate is also described.

4 Claims, 3 Drawing Sheets

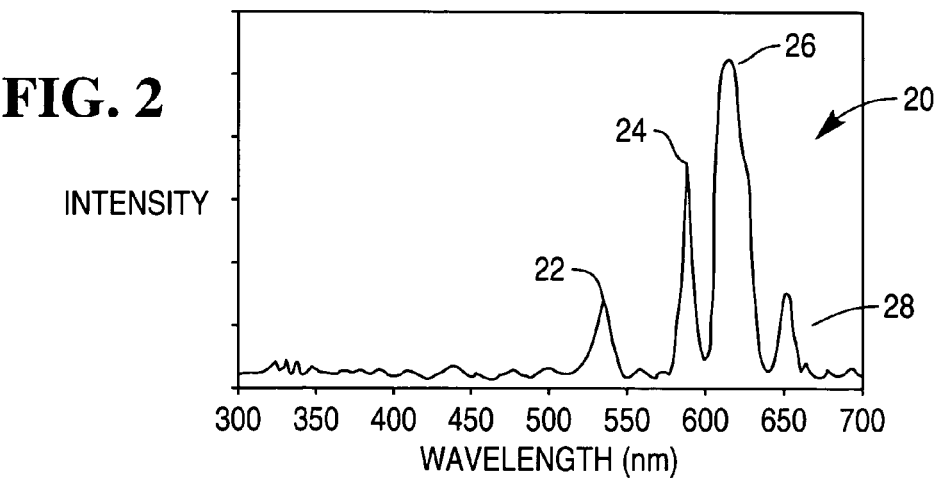
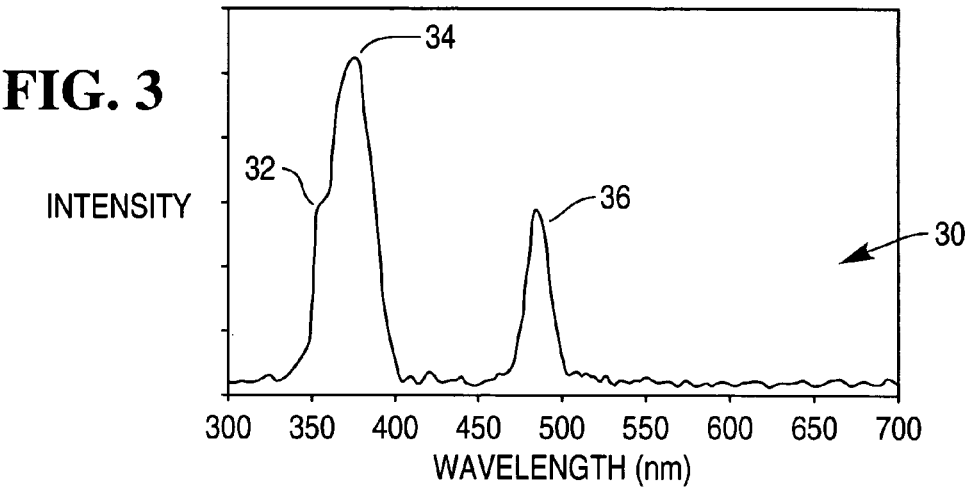
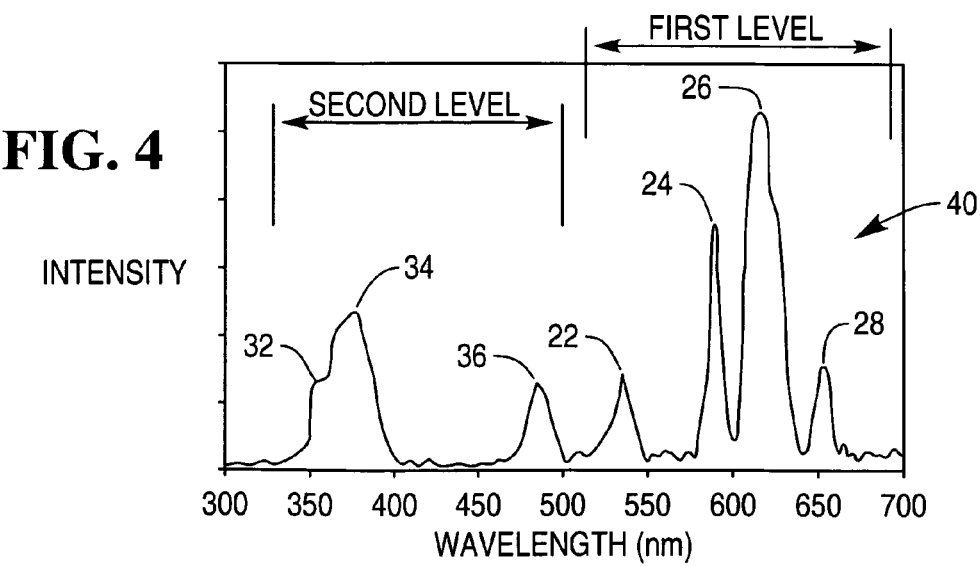

FIRST LEVEL CODE     SECOND LEVEL CODE

SECURE TAG CODING

The present invention relates to secure tag coding.

BACKGROUND

Secure tags are used for a number of different purposes; a primary purpose being preventing, detecting, and/or deterring counterfeiting.

One type of secure tag that has recently been developed is based on small particles of a rare earth doped host, such as glass. This type of secure tag is described in US patent application No. 2004/0262547, entitled "Security Labelling," and US patent application No. 2005/0143249, entitled "Security Labels which are Difficult to Counterfeit", both of which are incorporated herein by reference.

These rare earth doped particles (hereinafter "RE particles") can be applied to valuable items in different ways. For example, the secure tags can be incorporated in fluids which are applied (by printing, spraying, painting, or such like) to valuable items, or incorporated directly into a substrate (paper, rag, plastic, or such like) of the valuable items.

In response to suitable excitation, RE particles produce a luminescence spectrum having narrow peaks because of the atomic (rather than molecular) transitions involved. Luminescence is a generic term that relates to a substance emitting optical radiation in response to excitation, and includes photoluminescence, such as fluorescence and phosphorescence.

Fluorescent materials (dyes and pigments) tend to have a decay lifetime of $10^{-9}$ to $10^{-7}$ seconds (1 to 100 nanoseconds). The fluorescence disappears very quickly after excitation ceases. Thus, detecting fluorescence is typically performed simultaneously with excitation.

Phosphorescent materials (dyes and pigments) tend to have a decay lifetime of $10^{-3}$ to 100 seconds. Although detecting phosphorescence can be done simultaneously with excitation, it is also possible to measure phosphorescence after the excitation is removed, thereby adding to the security of a phosphorescent secure tag.

It would be desirable to have secure tags that include multiple levels (or layers) of codes. For example, it would be desirable to have a secure tag that luminesces at one or more fixed wavelengths to indicate that the secure tag is genuine, or owned by a particular company (the first level code); but also luminesces at one or more additional wavelengths to indicate a certain feature or quality of the substrate the secure tag is applied to (the second level code). Thus, different secure tags from the same company would have the same fixed wavelengths but different additional wavelengths.

The difficulty with achieving multiple levels of codes is that the luminescence from a secure tag is determined by the electronic states within that secure tag. When dopants are added to introduce luminescence at additional wavelengths, the luminescence from the fixed wavelengths change unpredictably. Thus, introducing a new dopant to provide a new second level of code may change the first level of code, thereby ruining the multi-level coding arrangement. This unpredictability means that the only reliable way to ensure that a new dopant does not affect the first level code (and thereby provide consistent multiple levels of codes) is by trial and error, which is expensive. If a large number of different second level codes are desired, it may not be feasible to use the trial and error approach.

SUMMARY

According to a first aspect of the present invention there is provided a secure tag coding method comprising: providing a first type of secure tag having a first luminescence profile to indicate a first level code; providing a second type of secure tag having a second luminescence profile different from the first luminescence profile to indicate a second level code; mixing secure tags of the first type with secure tags of the second type in a predetermined ratio so that excitation of the mixed secure tags produces a composite of the first luminescence profile and the second luminescence profile, from which composite a multi-level code can be ascertained; and applying the mixture of first and second types of secure tags to a substrate.

By virtue of this aspect of the invention, a multi-level code is provided in a single luminescence spectrum. As each luminescence profile results from a different secure tag, there is minimal interference between dopants in one type of tag and dopants in another type of tag.

The first level of code may be indicative of an originator of the substrate. The word "originator" is used in a broad sense and includes: a manufacturer, owner, creator, seller, distributor, issuer, provider, or such like. Each originator may be an individual, a company, a partnership, a government body, a non-government body, software, or such like. Each originator has a unique code (or possibly multiple codes), so that identification of the first level code may serve as validation of the authenticity of the substrate.

The second level of code may be selected from a plurality of possible codes for that originator. The second level of code may provide additional information about the substrate (for example, value, denomination, issuing state, issuing store, manufacturing location, product line, or such like), and there is typically multiple second level codes for each first level code. For different types of substrate from an originator, the first level code is typically the same for all substrates, but the second level code is different for different types of substrate.

The luminescence profile relates to pre-defined characteristics of a luminescence spectrum from a secure tag. The luminescence profile may include one or more of: presence or absence of emission at one or more wavelengths; presence or absence of a peak in emission at one or more wavelengths; the number of emission peaks within all or a portion of the electromagnetic spectrum (for example, ultraviolet radiation to infrared radiation (e.g., approximately 100 nm to 1 µm)); rate of change of emission versus wavelength, and additional derivatives thereof; rate of change of emission versus time, and additional derivatives thereof; absolute or relative intensity of emission at one or more wavelengths; ratio of an intensity of one emission peak to an intensity of another emission peak or other emission peaks; the relative intensities of all of the peaks; the shape of an emission peak; the width of an emission peak; or such like.

As used herein, a secure tag is a different type of secure tag to other secure tags if either (i) it has a different dopant, or combination of dopants, to all the other secure tags, or (ii) it has a different mol % of dopant or dopants to other secure tags, or (iii) it has a different host to other secure tags. For example, under (i) a secure tag having a borosilicate glass host doped with 3 mol % of Eu is a different type of secure tag to a secure tag having a borosilicate glass host doped with 3 mol % of Tb; under (ii) a secure tag having a borosilicate glass host doped with 3 mol % of Eu is a different type of secure tag to a secure tag having a borosilicate glass host doped with 2.9 mol % of Eu; and under (iii) a secure tag having a borosilicate glass host doped with 3 mol % of Eu is a different type of secure tag to a secure tag having a polymer host doped with 3 mol % of Eu. A different host, dopant type, or dopant concentration results in a different type of secure tag.

Mixing secure tags of the first type with secure tags of the second type may include mixing the two types of secure tags to ensure that the ratio of (i) the intensity of one or more emission peaks from the second luminescence profile, to (ii) the intensity of one or more emission peaks from the first luminescence profile, meets a predetermined criterion. This criterion may be a ratio that enables simultaneous measurement of both the first luminescence profile and the second luminescence profile. Alternatively, or additionally, the predetermined criterion may be related to the second level code. This is possible because although the luminescence profile of a secure tag is constant for that secure tag, the second level code may be related to the relative intensity of one or more peaks in the second luminescence profile to one or more peaks in the first luminescence profile. Similarly, but perhaps less desirably, the first level code may be related to the relative intensity of one or more peaks in the first luminescence profile to one or more peaks in the second luminescence profile. This may be less desirable because an originator may desire to have a multi-level code but only use the first level, so it would be preferably for such cases that the first level code is not related to a second level code, which may not be present.

Applying the mixture of the first and second type of secure tags to a substrate may include using the first and second type of secure tags as a pigment that is added to an ink. The ink may be optically clear or may include other pigments. Each type of secure tag may be carried by a different ink, so that secure tags could be mixed by mixing the different inks.

A third type of secure tag having a third luminescence profile to indicate a third level code may also be used. The concentration of the first, second, and third type of secure tags may be selected to ensure that all three levels of codes are detected. The concentrations may be balanced to compensate for different luminescence efficiencies of the three types of secure tags.

It should be appreciated that four or more types of secure tags may be used.

The word "substrate" is used herein in a broad sense, and may include materials such as metal, plastic, paper, rubber, card, wood, a combination of any of the preceding, or such like. The word "substrate" is not limited to a thin item, but includes items of any size or shape. A "substrate" may refer to a label applied to another item.

According to a second aspect of the present invention there is provided a substrate carrying a secure tag coding arrangement to provide multi-level codes, the substrate comprising: an illumination area; a first type of secure tag located within the illumination area at a first concentration and having a first luminescence profile to indicate a first level code; a second type of secure tag also located within the illumination area at a second concentration and having a second luminescence profile different from the first luminescence profile to indicate a second level code; the first and second type of secure tags being arranged to ensure that excitation anywhere within the illumination area produces a composite of the first luminescence profile and the second luminescence profile, from which composite a multi-level code can be detected.

According to a third aspect of the present invention there is provided a device for selecting and applying a secure tag coding arrangement to a substrate, the device comprising: a first hopper storing a first type of secure tag having a first luminescence profile to indicate a first level code; a second hopper storing a second type of secure tag having a second luminescence profile different from the first luminescence profile to indicate a second level code; a mixer coupled to both the first hopper and the second hopper and configured to control flow of the first type of secure tag and the second type of secure tag to allow adjustment of the concentration of each type of secure tag; and a processor coupled to the mixer for control thereof.

The device may include additional hoppers for different types of secure tags.

The device may include a fluid chamber coupled to the mixer so that the device ejects fluid containing first and second types of secure tags in a concentration determined by the processor.

The fluid may be a liquid, such as an ink, varnish, lacquer, paint, or such like. Alternatively, the fluid may be a gas, such as air, nitrogen, or such like.

By using separate secure tags for each level of code, interaction between dopants is minimized compared with a secure tag that attempts multi-level coding using multiple dopants. Using separate secure tags for each level of code ensures that a huge number of possible combinations are available. When this approach is applied to secure tags that can only accommodate a relatively small concentration of dopants (such as 6 mol %), this greatly increases the number of codes available. If the maximum concentration in one secure tag is 6 mol %, and six different dopants are used in that one secure tag, at dopant concentration steps of 0.1 mol %, then the potential number of codes is approximately two million. However, these aspects of the invention allow the full range (0.1 mol % to 6 mol %) for each of the six dopants, which yields a potential number of codes of approximately fifty-two billion. Although for practical reasons this number may never be reached, it offers far more permutations than using a single type of secure tag with multiple dopants.

By using separate secure tags for each level of code, it is comparatively simple to provide a first level code that is constant for a number of different substrates, and a second level code that can be varied by using different secure tags. This enables an originator to have a wide range of products, each type of product being identified by a unique second level code, but all sharing the same first level code.

These and other aspects of the present invention will be apparent from the following specific description, given by way of example, with reference to the accompanying drawings.

BRIEF DESCRIPTION OF THE DRAWINGS

In the accompanying drawings:

FIG. 2 is a graph illustrating a luminescence spectrum obtained from a first type of secure tags included in the substrate of FIG. 1;

FIG. 3 is a graph illustrating a luminescence spectrum obtained from a second type of secure tags included in the substrate of FIG. 1;

FIG. 4 is a graph illustrating a luminescence spectrum obtained from an illumination area of the substrate of FIG. 1, where the illumination area provides a composite luminescence spectrum with contributions from both the first and second type of secure tags;

DETAILED DESCRIPTION

Figure 1:
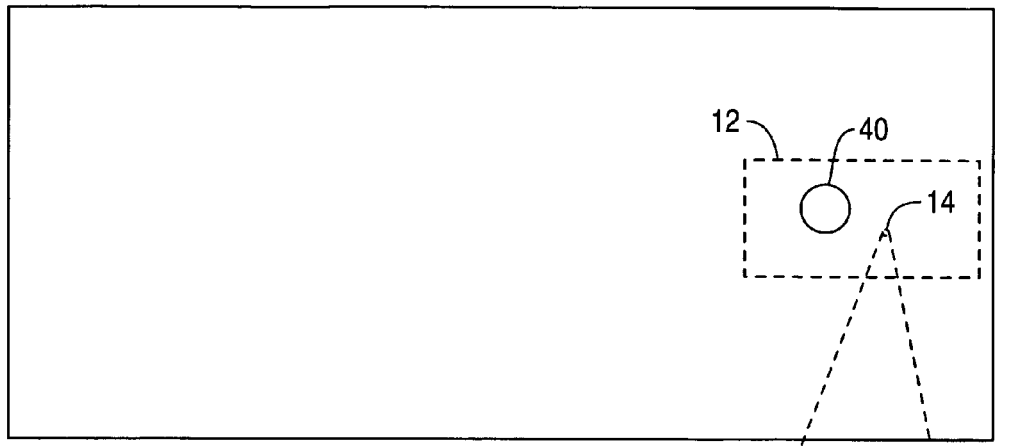
FIG. 1 is a schematic plan view of a substrate including a secure tag coding arrangement according to one embodiment of the present invention.

Reference is first made to FIG. 1, which is a schematic plan view of a substrate 10 including a secure tag coding arrangement according to one embodiment of the present invention. In this embodiment, the substrate 10 is in the form of a banknote.

The banknote 10 includes an illumination area 12, a portion of which is shown greatly enlarged in circle 14. The illumination area 12 includes two different types of secure tags 16a,16b. In this embodiment, both types of secure tags 16 are in the form of rare earth doped particles (RE particles). The tags 16 are relatively small, typically having a generally spherical shape and a diameter of approximately five microns. In FIG. 1, one type of secure tag 16a is illustrated as shaded; whereas, the other type of secure tag 16b is illustrated un-shaded. The two types of secure tags 16 have been mixed in a pre-determined ratio, as will be described in more detail below.

One type of secure tag 16a comprises 3 mol % Eu-doped borosilicate glass. When excited by UV light, this type of tag 16a has a luminescence spectrum 20 as shown in FIG. 2. This spectrum has peaks at approximately 535 nm (labelled 22), 590 nm (labelled 24), 615 nm (labelled 26), and 654 nm (labelled 28). The portion of the luminescence spectrum 20 from 510 nm to 700 nm includes all of these peaks, and comprises the luminescence profile for the secure tag 16a. This means that a large area of the luminescence spectrum 20 (below 510 nm and above 700 nm) is not part of the luminescence profile for that secure tag 16a.

The other type of secure tag 16b is a 3 mol % Tb-doped borosilicate tag. When excited by UV light, this type of tag 16b has a luminescence spectrum 30 as shown in FIG. 3. This spectrum 30 has peaks at approximately 354 nm (labelled 32), 375 nm (labelled 34), and 483 nm (labelled 36). The portion of the luminescence spectrum 30 from 300 nm to 510 nm includes all of these peaks, and comprises the luminescence profile for the secure tag 16b. This means that large areas of the luminescence spectrum 30 (below 300 nm and above 510 nm) are not part of the luminescence profile for that secure tag 16b.

Each of these two types of secure tags 16a,b has at least one peak that does not merge with a peak from the other secure tag. This enables the luminescent contribution from each secure tag 16 to be identified. In this example, none of the peaks from the Eu secure tag 16a merges with any of the peaks from the Tb secure tag 16b.

The emission from the Eu secure tags 16a is much stronger than the emission from the Tb secure tags 16b, so there is a greater preponderance of Tb secure tags 16b than Eu secure tags 16a in the illumination area 12. The tags 16 are mixed in such a way that a typical beamspot from an excitation source (which is typically at least 2 mm in diameter) excites the correct proportion of the first and second types of secure tags 16. This is illustrated in FIG. 1, where the circle 40 represents a typical beamspot. Although not to scale, this illustrates how the beamspot excites a mixture of the Eu and Tb secure tags 16.

FIG. 4 illustrates a luminescence spectrum 40 resulting from excitation of part of the illumination area 12 (which includes a predetermined mixture of Eu and Tb secure tags 16). It is apparent from FIG. 4 that the luminescence at lower wavelengths (300 nm to 510 nm) results from the Tb secure tags 16b (it comprises the Tb luminescence profile), and the luminescence at higher wavelengths (510 nm to 700 nm) results from the Eu secure tags 16a (it comprises the Eu luminescence profile). This enables two levels of coding to be used: a first level (indicative of issuance, ownership, origin, or such like) and a second level (indicative of type or some other factor, feature, quality, or such like).

In this example, the presence of peaks 22 to 28 indicates that the banknote 10 was issued by the US government (so the currency is US dollars), and the presence of peaks 32 to 36 indicates that the banknote 10 is a particular denomination (for example, a one hundred dollar bill). This provides a two-level code. The first level of code represents an originator (US government, which issues the currency), and is represented by the Eu secure tags 16a; whereas, the second level represents a feature of the currency (the denomination), and is represented by the Tb secure tags 16b.

The presence of the peaks from the Eu secure tags 16a (the Eu luminescence profile) may be used to validate the currency.

The presence of the peaks from the Tb secure tags 16b (the Tb luminescence profile) may be used to indicate the denomination.

Using a code that is based on the presence of peaks does not provide a huge number of permutations, so the code may be based on the relative intensities of the peaks to one another (which changes with the mol % of doping) or the relative intensity of one or more peaks in the Tb luminescence profile to one or more peaks in the Eu luminescence profile (which changes with the proportion of Eu secure tags 16a to Tb secure tags 16b). For example, the ratio of the intensity of peak 26 to the intensity of peak 34 (FIG. 4) may be used to determine the denomination.

This allows the coding arrangement to be controlled by adjusting the ratio of Tb secure tags 16b to Eu secure tags 16a in the illumination area 12 (FIG. 1). The greater the proportion of Eu secure tags 16a to the total number of secure tags 16, the higher the ratio of the intensity of peak 26 to peak 34. A low ratio of intensity of peak 26 to peak 34 may indicate a twenty dollar bill, a higher ratio may indicate a one hundred dollar bill, and so on.

Figure 5:
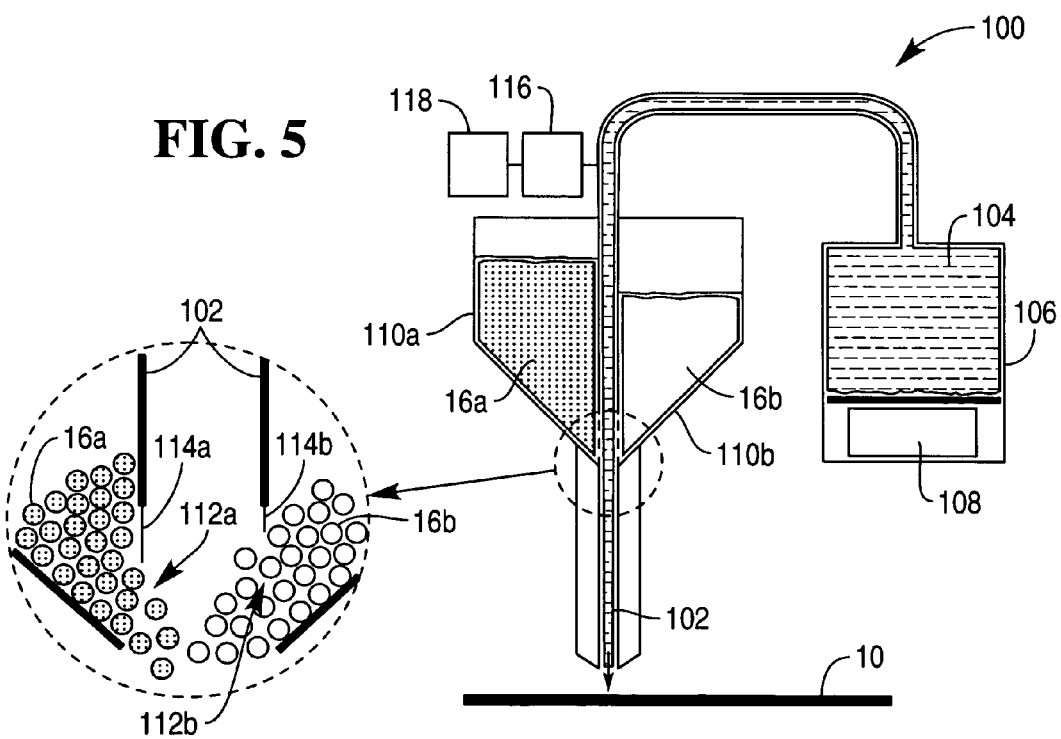
FIG. 5 is a schematic diagram of a device, according to another embodiment of the invention, for selecting and applying a secure tag coding arrangement to the substrate of FIG. 1.

Reference will now be made to FIG. 5, which is a simplified schematic diagram of a device 100, according to another embodiment of the invention, for selecting and applying a secure tag coding arrangement to the substrate of FIG. 1.

The device 100 has opposing sidewalls 102 that define a nozzle through which a mixture of clear ink 104 and secure tags 16 is ejected. The clear ink 104 is stored in a fluid chamber 106 (in the form of a reservoir) including a pump 108 for expelling the clear ink from the reservoir 106 through the nozzle and onto the substrate 10. The device 100 also includes a hopper 110a that stores Eu secure tags 16a, and a hopper 110b that stores the Tb secure tags 16b. Each hopper 110 has a throat 112, including a throttle-valve 114, which controls the flow rate of secure tags 16 from the hopper 110 into the nozzle. A processor 116 controls the position of the throttle valves 114a,b to determine the proportion of each type of secure tag 16. The processor 116 controls the position of the throttle valves 114a,b in response to a user selection made on an input mechanism 118 in the form of switches. A user moves the switches 118 to a desired position to select the desired ratio of Eu secure tags 16a to Tb secure tags 16b. This device 100 allows a user to implement a two level coding arrangement, and to select a desired code within this arrangement by moving the switches 118. The switches may include text describing the particular coding arrangement implemented by that configuration of switches.

Figure 6A:
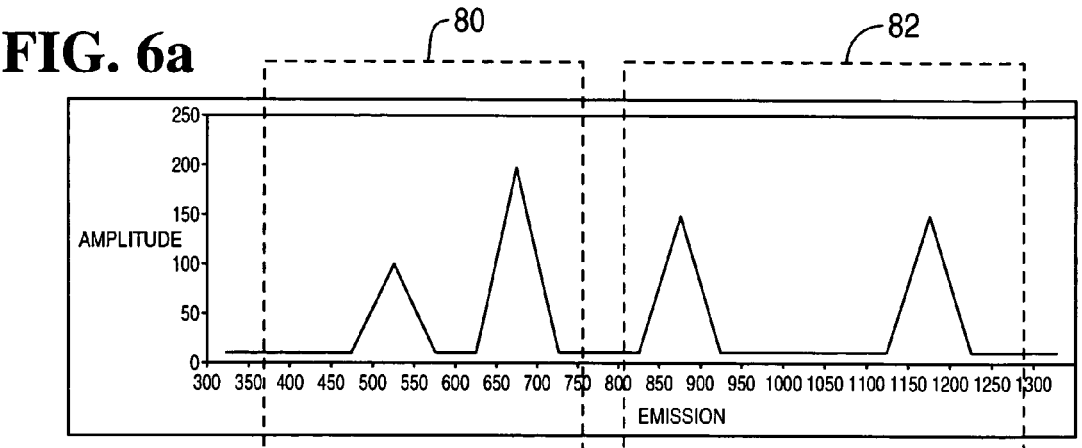
FIGS. 6a to 6c are graphs illustrating luminescence spectra obtained from three different types of substrate, all from the same originator, and each having a different second level code.
Figure 6B:
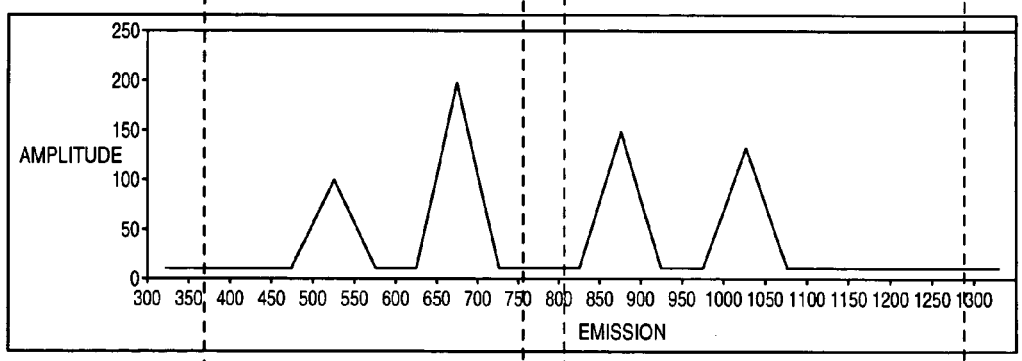
Figure 6C:
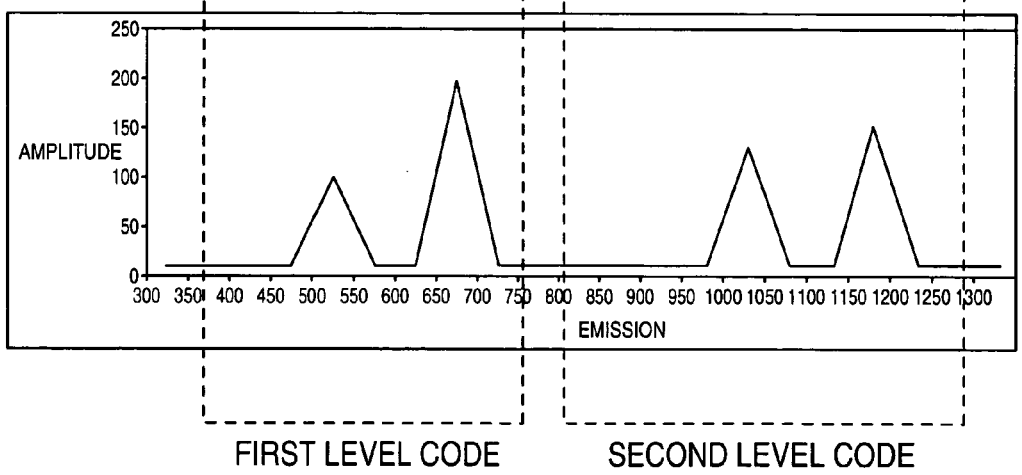

Reference will now be made to FIGS. 6a to 6c, which are graphs illustrating luminescence spectra obtained from three different types of substrate, all from the same originator (having the same first level code 80), and each having a different second level code 82. As can be seen from FIGS. 6a to 6c, the second level code may be based on different peaks occurring at different wavelengths.

Various modifications may be made to the above described embodiments within the scope of the present invention, for example, in other embodiments, the substrate may be a different form of sheet media (such as a ticket, a receipt, a time card, an identification card, a bank card, a credit card, or such like), or a non-sheet media item (such as a pen, an automobile, a bicycle, a chair, or such like).

In other embodiment, more than two different types of secure tags 16 may be used. The secure tags 16 may be luminescent tags that are not based on rare earth doped particles, or may be tags that emit a particular energy that is not photon-based. In other embodiments, the tags 16 may be smaller or larger than five microns, and may not have a non-spherical shape (such as an irregular shape, or a regular shape such as a diamond shape).

In the above embodiment, the location of the peaks comprises the luminescence profile for the secure tag; in other embodiments, the location and/or the intensity of one or more peaks may comprise the luminescence profile for a secure tag.

In the above embodiment the peaks at higher wavelengths indicated a fixed criterion, namely the origin of the substrate (that is, the currency); and the peaks at the lower wavelengths indicated a variable criterion, namely a feature of that substrate (that is, the denomination). In other embodiments (like that shown in FIGS. 6a to 6c), the peaks at higher wavelengths may indicate the variable criterion and the peaks at lower wavelengths may indicate the fixed criterion; alternatively, peaks representing the fixed criterion and peaks representing the variable criterion may be distributed across the luminescence spectrum, so that a peak representing the fixed criterion may be at a higher wavelength than one peak representing a variable criterion, and at a lower wavelength than another peak representing a variable criterion. In other embodiments, there may only be one peak for the fixed criterion and/or one peak for the variable criterion. In some embodiments, the relative peak intensities may be used to determine the multi-level coding arrangements.

In other embodiments, the device 100 may operate according to different principles, for example, the device 100 may electrostatically charge the secure tags 16, and the tags may be applied separately to the application of a clear ink. Thus, the clear ink may be deposited on the substrate prior to, or after, the secure tags are deposited, rather than simultaneously with the secure tags. In such embodiments, the device may not include a clear ink reservoir. In other embodiments, an adhesive may be used instead of a clear ink. In other embodiments, more than two hoppers may be used.

In other embodiments the input mechanism 118 may be a keypad, one or more dials, a sliding selector, or any other convenient input mechanism.

In other embodiments, each type of secure tag may be incorporated into its own ink. These different inks may be mixed to create the multi-level code arrangement. The proportion of each ink being determined by the required proportion of the secure tag carried by that ink. This may have advantages where it is easier to apply multiple different inks than to use a device similar to that described with reference to FIG. 5. These multiple different inks may be applied, for example, using a printer that operates using similar principles to the operation of an ink jet printer.

What is claimed is:

1. A secure tag coding method comprising:
providing a first type of secure tag having a first luminescence profile to indicate a first level code;
providing a second type of secure tag having a second luminescence profile different from the first luminescence profile to indicate a second level code;
mixing secure tags of the first type with secure tags of the second type in a predetermined ratio to produce a mixture so that excitation of the mixture produces a composite of the first luminescence profile and the second luminescence profile, from which composite a multi-level code can be ascertained, the mixture at the predetermined ratio enables simultaneous measurement of both the first luminescence profile and the second luminescence profile and mixing the two types of secure tags to ensure that the ratio of (i) the intensity of one or more emission peaks from the second luminescence profile, to (ii) the intensity of one or more emission peaks from the first luminescence profile, meets a predetermined criterion, the predetermined criterion is a ratio that enables simultaneous measurement of both the first luminescence profile and the second luminescence profile, wherein the second level code is related to the relative intensity of the one or more emission peaks from the second luminescence profile to the one or more emission peaks from the first luminescence profile; and
applying the mixture of first and second types of secure tags to a substrate.

2. The method of claim 1, wherein applying the mixture of the first and second type of secure tags to a substrate includes using the first and second type of secure tags as a pigment that is added to an ink.

3. The method of claim 1, further comprising providing a third type of secure tags having a third luminescence profile different from the first and second luminescence profiles to indicate a third level code.

4. The method of claim 1, wherein mixing secure tags of the first type with secure tags of the second type includes balancing the concentrations of the first type and the second type to compensate for different luminescence efficiencies of the two types of secure tags.

* * * * *